United States Patent [19]

Yanagisawa et al.

[11] Patent Number: 5,168,068

[45] Date of Patent: Dec. 1, 1992

[54] ADSORBENT-TYPE GAS MONITOR

[75] Inventors: Yukio Yanagisawa, Wayland, Mass.; Masakazu Hishinuma, Yokohama, Japan

[73] Assignee: President and Fellows of Harvard College, Cambridge, Mass.

[21] Appl. No.: 369,319

[22] Filed: Jun. 20, 1989

[51] Int. Cl.$^5$ .............................................. G01N 31/22
[52] U.S. Cl. ...................................... 436/134; 422/56; 422/57; 422/58; 422/88; 436/167
[58] Field of Search .................................. 422/56-58, 422/88; 436/134, 167

[56] References Cited

U.S. PATENT DOCUMENTS

| | | |
|---|---|---|
| 601,791 | 4/1898 | Flood et al. |
| 2,337,232 | 12/1943 | Daly |
| 2,409,928 | 10/1946 | Cahenzli, Jr. |
| 2,600,435 | 7/1952 | Shapiro |
| 2,798,109 | 7/1957 | Voight |
| 3,507,623 | 4/1970 | McConnaughey |
| 3,582,274 | 6/1971 | Keyes ............................. 436/167 X |
| 3,969,095 | 7/1976 | Kurahashi |
| 4,019,879 | 4/1977 | Rabo et al. |
| 4,019,880 | 4/1977 | Rabo et al. |
| 4,177,048 | 12/1979 | Rivers et al. |
| 4,306,894 | 12/1981 | Fukami et al. |
| 4,783,316 | 11/1988 | Pannwitz ....................... 436/902 X |

OTHER PUBLICATIONS

Palmes et al., Analitical Chemistry, 51:2400-2401, 1979.
Palmes et al., American Industrial Hygiene Association Journal 34:78-81, 1973.
Lambert et al., Environ. Sci. Technol. 21:500-503, 1987.
Yanagisawa et al., Environment International 8:235-242, 1982.
Palmes et al., Am. Ind. Hyg. Assoc. J. 37:570-577, 1976.
Hirai et al., Chemistry Letters, The Chemical Society of Japan, pp. 361-364, 1983.
Egerton et al., J. Chem. Soc. Faraday Trans. 69(1):22-38, 1973.
"Gas Monitoring Badges-Guide to Sorbent Capsule Selection," SKC, Inc. Catalog, p. 41, 1984.
Gonzalez et al., Amn. Ind. Hyg. Assoc. J., 44:514-520, 1983.
Gentry et al., Am. Ind. Hyg. Assoc. J., 48:287-292, 1987.

Primary Examiner—Jill A. Johnston
Attorney, Agent, or Firm—Fish & Richardson

[57] ABSTRACT

A passive gas sampling apparatus for detecting an analyte gas, which apparatus includes (1) a shell enclosing an adsorbent and (2) a diffusion tube extending through the shell and having (a) an inlet opening means outside the shell, through which the analyte gas may enter the diffusion tube, and (b) an outlet opening imbedded in the adsorbent inside the shell; and a method for using such apparatus.

2 Claims, 2 Drawing Sheets

ADSORBENT-TYPE GAS MONITOR

BACKGROUND OF THE INVENTION

This invention relates to gas monitors.

Investigation of the levels of various pollutants in ambient air requires a reliable means of sampling the air and quantitatively determining the concentration of the pollutant of interest. Although pump-driven air sampling techniques are frequently employed, the passive type of sampler, which relies upon molecular diffusion of gases, has proven to be comparatively simple, lightweight, easy to use, inexpensive and nonhazardous, and therefore more suitable for certain applications. Multiple passive samplers can be used to make simultaneous multi-point measurements or repeated measurements over time at a single location, and are therefore an important tool for large-scale air pollution studies involving wide temporal or spatial variables. Also, the passive design may be incorporated into a device intended to monitor an individual's personal exposure to a given pollutant over a period of time.

Generally, the passive gas sampler consists of a collection apparatus containing a collecting medium. The apparatus is typically a container with an orifice at one end to permit ambient gases to diffuse in and thereby contact the collecting medium. Insertion of a tube through the orifice and part way into the container permits the diffusion rate, which is proportional to the cross-sectional area of the diffusion path and inversely proportional to its length, to be reduced without reducing the surface area of collecting medium used (Palmes et al., Am. Ind. Hyg. Ass. J. 34:78-81, 1973; Palmes et al., Anal. Chem. 51:2400-2401, 1979).

The collecting medium may be in either liquid or solid form. The liquid type, which may be coated onto a mechanical support, typically absorbs the pollutant gas by chemically reacting with it. An example of a liquid reagent is triethanolamine, widely used to collect $NO_2$ (e.g., Palmes et al., Am. Ind. Hyg. Ass. J. 37:570-577, 1976; Yanagisawa et al., Environ. Int. 8:235-242, 1982).

The solid type of collecting medium commonly traps the molecules of pollutant gas by adsorption. Activated charcoal, frequently used in gas monitors to collect benzene and other kinds of organic vapors, is one such solid adsorbent. Adsorbed gas may be recovered from the solid adsorbent by extraction with an appropriate solvent, by reducing atmospheric pressure on the adsorbent, or by heating the adsorbent until the gas is released ("thermal desorption").

Passive samplers specifically designed to determine the level of carbon monoxide in ambient air have included two kinds of direct-read dosimeters: a degree-of-color-change device, in which carbon monoxide permeating a thin bed of colorimetric granular indicator changes the color of the indicator to a degree dependant upon the dose of carbon monoxide adsorbed (U.S. Pat. No. 3,507,623); and a length-of-stain device, in which carbon monoxide diffusing lengthwise through a bed of inert carrier impregnated with an indicator generates a color change along the diffusion path, the length of which is proportional to the concentration of the gas and the sample time (McConnaughey et al., Am. Ind. Hyg. Assoc. J. 46:357-362, 1985). Indicators which change color when exposed to carbon monoxide have typically utilized either palladium(II) or silver compounds (Lambert et al., Environ. Sci. Technol. 21:500-503, 1987).

SUMMARY OF THE INVENTION

In general, the invention features a device for detecting an analyte gas in a mixture of gases. The device comprises a container or "shell" holding a layer of adsorbent capable of adsorbing the analyte gas, and a diffusion tube extending into the container with (1) an outlet opening imbedded in the adsorbent layer and (2) an inlet opening, or a means of creating an inlet opening, in the part of the diffusion tube that projects outside the container, through which diffusion tube, when the openable end is opened, the analyte gas may diffuse from the atmosphere outside the container directly into the adsorbent layer.

In preferred embodiments,

1. The diffusion tube is sealed except for the openable inlet opening outside the container and the outlet opening imbedded in the adsorbent layer; which openable inlet opening is preferably a sealed section of the diffusion tube and a means for creating an opening in the sealed section;

2. The outlet opening is at the tip of one end of the diffusion tube and the inlet opening, when opened, is at the tip of the opposite end of the diffusion tube;

3. The length and minimum interior cross-sectional area of the diffusion tube are selected so that the maximum rate of diffusion of the analyte gas along the diffusion tube is less than 50%, and more preferably less than 10%, of the maximum rate that the analyte gas could diffuse into the apparatus in the absence of the diffusion tube and its connector (i.e., the mechanism(s) which holds the diffusion tube in place in the apparatus and seals the end of the apparatus through which the diffusion tube passes), such minimum interior cross-sectional area being herein defined as the smallest interior cross sectional area which may be derived by measuring at any given point along the length of the diffusion tube, and at any angle to the long axis of the diffusion tube: for a straight-sided tube of uniform inner diameter (i.d.), this would be the cross sectional area perpendicular to the long axis of the diffusion tube, and could be expressed as $$\pi \left( \frac{i.d.}{2} \right)^2;$$

4. The container is a cylinder, closed at both ends, with the diffusion tube extending through one closed end;

5. The analyte gas is carbon monoxide and the mixture of gases in the gas sample includes water vapor;

6. The adsorbent is a zeolite, more preferably a multivalent-cation-exchanged zeolite, and most preferably a zeolite Y, e.g., Zn-Y zeolite, Mn-Y zeolite, Cu-Y zeolite, $UO_2$-Y zeolite or Ni-Y zeolite, and most preferably Zn-Y zeolite;

7. The apparatus is adapted to be worn by an individual or, alternatively, to be a stationary monitor.

Also featured is a gas sampling apparatus designed to measure the concentration of carbon monoxide in a gas sample, such apparatus having zeolite, more preferably a multivalent-cation-exchanged zeolite and most preferably a zeolite Y (e.g., Zn-Y zeolite, Mn-Y zeolite, Cu-Y zeolite, $UO_2$-Y zeolite, or Ni-Y zeolite), as an adsorbent.

Also featured is a method of using the gas sampling apparatus to determine the presence or, alternatively, the concentration of an analyte gas, preferably carbon monoxide, in a gas sample, by exposing the opened inlet of the diffusion tube to the gas sample for a known period of time and analyzing the adsorbent for the presence or, preferably, the amount, of analyte gas adsorbed, preferably by subjecting the adsorbent to conditions whereby the adsorbed analyte gas is released from the adsorbent, most preferably by thermal desorption, and measuring the amount of analyte gas so released, most preferably by passing the released gases over a gas chromatographer, catalytically reducing the separated carbon monoxide, and determining, by means of a flame ionization detector, the molar amount of carbon monoxide so reduced.

The apparatus of the invention is a passive gas sampling device designed to permit the collection of one component of a gas mixture for subsequent measurement. The design of the device features (1) a diffusion tube along which the analyte gas is permitted to diffuse from the gas source at a controlled rate, which rate is determined by the dimensions of the diffusion tube, and (2) a layer of adsorbent in which is imbedded the outlet opening of the diffusion tube (the opening from which the diffusing analyte gas exits the tube). Analyte gas exiting the outlet opening is readily adsorbed by the adsorbent immediately adjacent to the outlet opening, and from there will diffuse, albeit relatively slowly, throughout the adsorbent matrix. The concentration of analyte gas, expressed as C, in the gas sample may be calculated from the amount of analyte gas collected (W) over a given exposure period (t), as follows:

$$W = S \cdot C \cdot t \qquad \text{eq. (1)}$$

where:

W = mass of sample collected by adsorbent (mole)
S = sampling constant (mole/ppm·hr)
$\Delta C$ = driving force (ppm) = $C - C'$
S C = sampling rate (mole/hr)
t = exposure time (hr)

The sampling constant S is a function of the diffusion coefficient of the analyte gas and the length and cross-sectional area of the diffusion path:

$$S = 3600 \left( \frac{DA}{LRT} \right) \qquad \text{eq. (2)}$$

where:

D = diffusion coefficient (cm$^2$/sec)
A = cross-sectional area of the diffusion path (cm$^2$)
L = length of the diffusion path (cm)
R = gas constant (erg/mol·K)
T = temperature (K)

The driving force $\Delta C$ is the difference between the concentration of analyte gas at the inlet opening of the diffusion tube (C) and that at the outlet opening (C'). As long as all molecules of analyte gas exiting the diffusion tube at the outlet opening are immediately adsorbed by the adsorbent, C' can be assumed to be zero and $\Delta C$ will be equivalent to C, permitting C to be calculated from known values for W, S and t. If the rate of diffusion of the analyte gas along the tube is greater than its rate of diffusion throughout the adsorbent matrix, then the adsorbent sites immediately adjacent to the outlet opening will eventually become saturated with the analyte gas molecules, the concentration of analyte gas at the imbedded outlet opening (C') will rise, and $\Delta C$ will fall correspondingly; $\Delta C$ will cease to be equivalent to C. This effect will be exacerbated if a second type of gas present in the sample gas mixture competes for the same adsorbent sites as does the analyte gas.

It therefore is important to limit the rate of diffusion along the diffusion tube, accomplished in one aspect of the invention by manipulating the length and inner diameter of the diffusion tube (i.e., the longer the tube and the narrower its inner diameter, the lower is the rate of diffusion along the tube). If the diffusion rate along the diffusion tube is kept low enough, saturation of adsorption sites at the outlet opening, by the analyte gas as well as by competing gases, can be minimized, and C' will remain approximately zero throughout the sampling period. Further, a lower diffusion rate along the diffusion tube means that a larger total mass of the analyte gas can be adsorbed by the device and diffused through the adsorbent matrix before the sites adjacent the outlet opening are saturated, making the device more sensitive to low ambient levels of the analyte gas.

In the same context, it is also important to maximize the diffusivity of the adsorbent, as well as its ability to trap molecules of analyte gas exiting the outlet opening. These are accomplished by imbedding the outlet opening of the diffusion tube in the adsorbent layer so that diffusion within the adsorbent matrix may occur in three dimensions from the point of the outlet opening, and by carefully choosing an appropriate type of adsorbent material.

In one preferred embodiment of the invention, the analyte gas is carbon monoxide and the adsorbent is Zn-Y zeolite. Zn-Y zeolite exhibits several advantageous qualities for this purpose, including a relatively high adsorption capacity for carbon monoxide, an ability to release the gas with high recovery efficiency when heated sufficiently, and a low incidence, during thermal desorption, of decomposition of the adsorbent (or of organic compounds adhering to the adsorbent) into a carbon monoxide artifactual by-product that would swamp the measurement of actually adsorbed carbon monoxide. These advantages give the carbon monoxide sampler of the invention a superior sensitivity, greater dynamic range, and improved accuracy within that range. In addition, an automated analyzer to perform the thermal desorption and quantitative analyses of released gas from large numbers of such samplers would be feasible, and would make large-scale, highly accurate studies relatively easy.

Other features and advantages of the invention will be apparent from the following description of the preferred embodiments thereof and from the claims.

DESCRIPTION OF THE PREFERRED EMBODIMENTS

The drawings are first described.

DRAWINGS

EXAMPLE 1

Particle size distribution of Na-Y zeolite adsorbent (LZY-52, Union Carbide Corporation, Linde Division, Sudbury, Mass.) was controlled by using sieves in sizes ranging from 20-35 mesh. The procedure employed for the $Zn^{2+}$ partial ion exchange was a modification of the procedure of Egerton et. al., J. Chem. Soc., Faraday Trans. 69:22-38, 1973. The Na-Y zeolite adsorbent (20 g) was first washed with a sodium acetate + acetic acid buffer (pH 5), and then, with 3 ml of the buffer solution, was put into 500 ml of 0.2M ZnCl aqueous solution and heated at 100° C. for 2 hrs. The zeolite was then filtered out of the ZnCl solution, washed with deionized water, dried overnight at 70° C., and stored over saturated ammonium chloride solution for three weeks. Finally the zeolite was calcined at 500° C. for 5 hrs.

Figure 1:
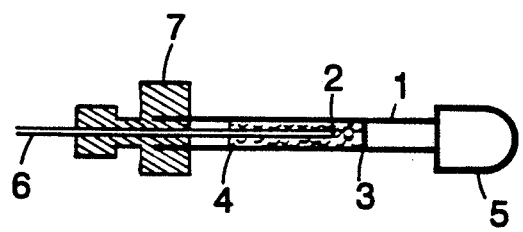
FIG. 1 is an illustration of one embodiment of the invention.

As illustrated in FIG. 1, the Zn-Y zeolite (110 mg) was packed in the center of a glass tube 1 (o.d.=6.35 mm, i.d.=4 mm, length=65 mm), forming a column 2 of packed zeolite 15 mm long which was held in place in the center of the tube by a stainless steel screen 3 on one end and glass wool 4 on the other. The packed zeolite was outgassed and dehydrated by heating at 400° C. for 5 minutes with an electric current applied to a nickel-chromium wire coiled around the glass tube of the sampler. Then one end of the glass tube was sealed by a rubber cap 5; the tip of a stainless steel tube 6 (o.d.=1.6 mm, i.d.=0.79 mm, length=60 mm) was inserted through the other end of the glass tube into the center of the adsorbent layer, and fixed into position with a reducing union and Teflon ferrules 7.

EXAMPLE 2

The pre-treated samplers were exposed to a known concentration of carbon monoxide in an exposure chamber for a predetermined period of time. The carbon monoxide concentration was kept constant at 105 ppm by using a commercially available mixed gas of carbon monoxide and nitrogen (Matheson Company, Gloucester, Mass.). Temperatures were controlled within ±2° C. by placing the exposure chamber in an incubator (Model-815, GCA Corp., Chicago, Ill.).

Figure 2:
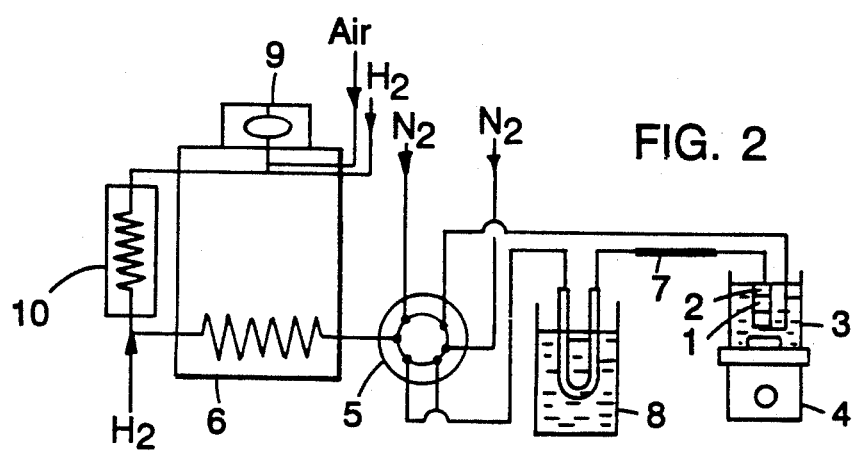
FIG. 2 is a schematic diagram of the thermal desorption system utilized by one embodiment of the invention.

After exposing the samplers to the mixed gas, analysis of carbon monoxide gas adsorbed by the samplers was carried out by thermal desorption followed by gas chromatography. A schematic diagram of the analytical instrumentation is shown in FIG. 2. The adsorbent layer 1, still packed in the glass tube 2, was heated by immersing it for 1 minute in an 80° C. water bath 3 over a magnetic stirrer 4. Then a 6-port valve 5 was switched to permit the desorbed gases released from the adsorbent to flow into the gas chromatographer 6 (Shimadzu GC-8). An alkaline trap 7 filled with lithium hydroxide and a cold trap 8 cooled by dry ice-methanol were installed in order to remove hydrochloric acid, water and heavy hydrocarbons which might have contaminated the desorption gases. Since the flame ionization detector 9 (FID) used was sensitive to methane but not to carbon monoxide, a methanator 10 was attached to the gas chromatographer (Shimadzu GC-8), in order to reduce carbon monoxide to methane. The methanator was a stainless steel tube (o.d.=3.18 mm, length=900 mm) packed with nickel catalyst (Gaschro, Kogyo) and held at 450° C.; hydrogen was supplied at a flow rate of 10 ml/min.

EXAMPLE 3

Figure 3:
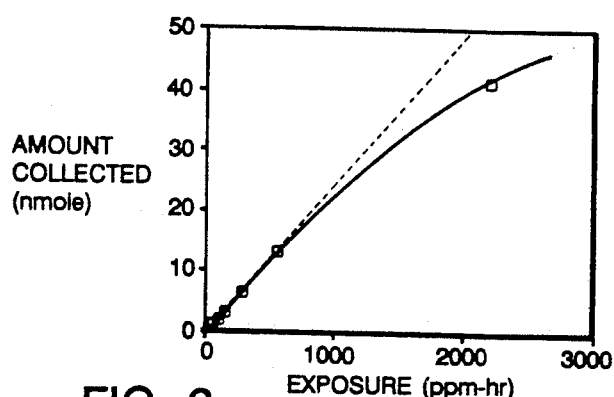
FIG. 3 is a graph illustrating the relationship between the exposure of the apparatus of the invention to carbon monoxide, and the amount of carbon monoxide recovered from the apparatus.

Samplers were exposed to a standard gas containing a carbon monoxide concentration of 105 parts per million (ppm) at 27° C. for up to 21 hours. FIG. 3 shows the relationship between the exposure (expressed as "ppm·hr": concentration in parts per million, times hours of exposure at that concentration), and the quantity of carbon monoxide recovered from the adsorbent. A linear relationship was observed for exposures up to 550 ppm·hr.

The sampling rate (S C) calculated from the linear portion of slope was $2.54 \times 10^{-9}$ mol/hr. However, the amount of carbon monoxide collected at an exposure of 2200 ppm hr was 27% less than the expected value calculated from a sampling rate of $2.54 \times 10^{-9}$.

The decreasing rate of carbon monoxide collection observed after 550 ppm·hr of exposure (i.e., at 2200 ppm·hr, a 27% lower than expected value) is ascribed to a decrease in the driving force ($\Delta C$), attributable to an increase in the concentration of carbon monoxide at the outlet opening of the diffusion tube as the adsorbent matrix adjacent to the outlet opening of the diffusion tube begins to exhibit saturation effects.

The apparent diffusion coefficient of carbon monoxide was calculated to be $D_{CO}=0.205$ by substitutions in eq. (2) of $S=2.42\times 10^{-11}$, $A=4.90\times 10^{-3}$, $L=6$, $R=8.31\times 10^{7}$, $T=300$. This apparent diffusion coefficient of carbon monoxide is comparable to the molecular diffusion coefficient of carbon monoxide estimated from Hirschfelder's equation: $D_{CO}=0.198$ (Hirschfelder et al., Molecular Theory of Gases and Liquids, John Wiley & Sons, New York, 1954).

EXAMPLE 4

Figure 4:
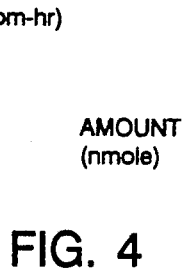
FIG. 4 is a graph illustrating the temperature dependence of the collection rate, where the carbon monoxide exposure is fixed at 105 ppm for 40 minutes.

Two different temperature effects are expected to influence carbon monoxide collection. The diffusion coefficient of an ideal gas is theoretically proportional to the 1.5th power of absolute temperature. Therefore, increasing temperature may cause an increase in the sampling rate due to an increase in the diffusion coefficient (eq.(2)). However, an increase in temperature also causes a decrease in the adsorption capacity of the adsorbent and a resulting increase in the carbon monoxide concentration (C') at the outlet opening of the diffusion tube, thereby decreasing the driving force ( C). The effect of temperature was examined by varying the exposure temperature between 5° C. and 35° C. As shown in FIG. 4, the amount of carbon monoxide collected by the sampler at 35° C. was 25% less than that collected at 5° C., indicating that, in the range of temperatures studied, the effect of temperature on the adsorption capacity of the zeolite is more significant than its effect on the diffusion coefficient of carbon monoxide.

EXAMPLE 5

Figure 5:
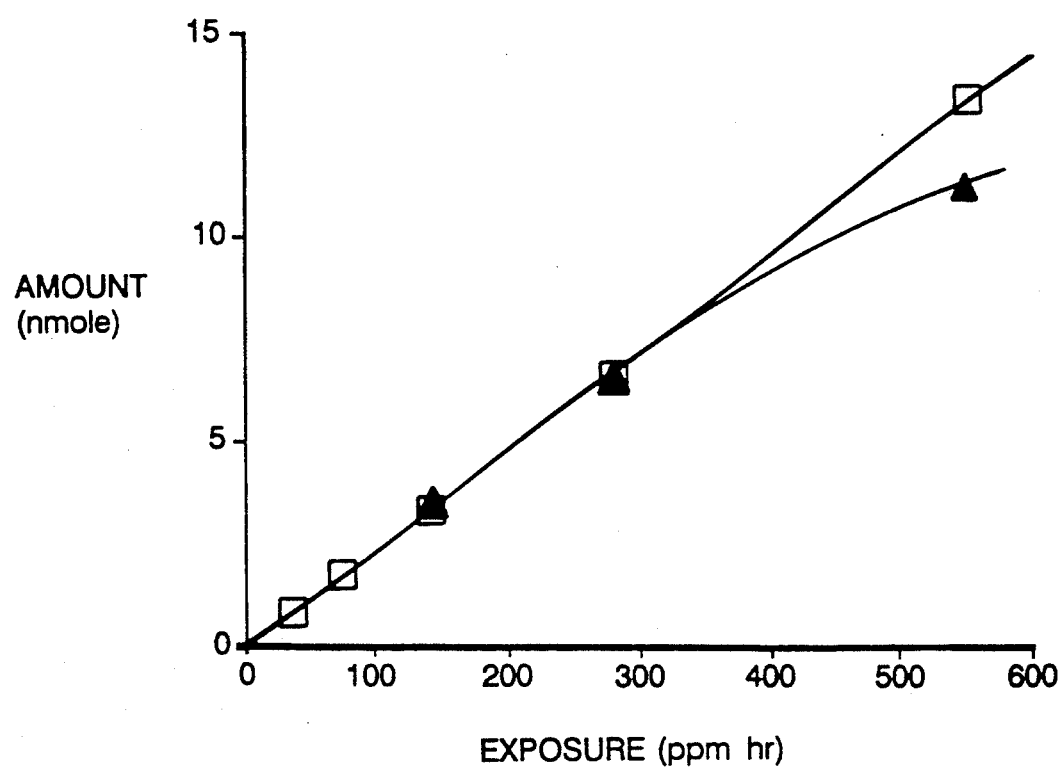
FIG. 5 is a graph illustrating a comparison of the effect of differing humidity levels during the exposure period on the amount of carbon monoxide recovered from the exposed apparatus.

Because ambient air typically contains a significant amount of water vapor and water is strongly adsorbed on Y-type zeolite, the presence of water vapor could theoretically interfere with the adsorption of carbon monoxide by the sampler. In order to assess the practicality of the carbon monoxide sampler of the invention for use under typically humid conditions, samplers were stored for 24 hrs over a saturated aqueous solution of ammonium sulfate, which kept the relative humidity at 80%, and then exposed to a gas mixture with 105 ppm carbon monoxide humidified at a relative humidity of 80% (achieved with the use of a saturated ammonium sulfate aqueous solution in the bottom of the chamber where the mixed gas was introduced). FIG. 5 shows the comparison between the amount of carbon monoxide collected on samplers stored and exposed under conditions of 80% humidity, and the amount collected under conditions of approximately 0% humidity. Up to an exposure of 300 ppm·hr, no significant difference was observed. However, at an exposure of 550 ppm·hr, a decrease of about 15% was observed in the amount of carbon monoxide adsorbed under 80% humidity, compared to the amount adsorbed under dry conditions. The eventual decrease in the sampling rate under conditions of high relative humidity may be attributable to a premature saturation of adsorption sites available on the zeolite, due to the competitive adsorption of water and carbon monoxide.

EXAMPLE 6

The stainless steel diffusion tube of the sampler of Example 1 may be replaced with a rigid plastic tube having a sealed tip extending outside the apparatus, which would prevent any gases from diffusing into the diffusion tube during storage of the apparatus, thus preserving the adsorbent for use when needed. The sealed plastic tip may be scored in such a way as to permit the tip to be snapped off at a predetermined point on the diffusion tube at the time that sampling is to begin.

OTHER EMBODIMENTS

Other embodiments are within the following claims. For example, adsorbents other than Zn-Y zeolite, such as another multivalent-cation-exchanged zeolite or similar material, may be used to collect carbon monoxide. By the use of an appropriate adsorbent and appropriate adjustments to the dimensions of the diffusion tube to control the rate of diffusion in the tube, the concentration of another gas of interest may be determined: for example, activated carbon may be utilized as an adsorbent to collect benzene vapor in the sampler of the invention. The amount of gas so collected may be measured by means other than thermal desorption and gas chromatography: for example, by extraction with a solvent and detection by light absorbance at an appropriate wavelength of light. The geometry of the collection apparatus may be varied by, for example, changing the dimensions of the diffusion tube or the outer shell of the sampler, or bending the diffusion tube.

The construction materials used in the apparatus may be varied: for example, the glass tube may be replaced with a tube of metal or plastic, while plastic, glass or non-stainless steel metals may substitute for the stainless steel of the diffusion tube.

The inlet opening of the diffusion tube may be temporarily sealed to preserve the adsorbent during storage, for example by threading the tip and screwing on a removable cap, by sealing the tip with a breakable seal, or by plugging the opening with a removable plug. The sealed inlet opening may be designed to be opened, for example, by snapping off a section of the diffusion tube at a pre-scored line or by inserting the sealed tip of the diffusion tube into a device which cuts, breaks or otherwise opens the tube at a predetermined point.

The apparatus may be adapted to be worn by an individual: for example, by constructing it out of unbreakable materials and attaching a pocket clip or other fastening means; or to function as a stationary monitor: for example, by attaching a loop for hanging from a hook, or a stake for inserting into the ground, or a stable support for a freestanding monitor. The overall size of the sampler may be increased or decreased as appropriate.

We claim:

1. A method of determining the concentration of carbon monoxide in a gas sample, said method comprising:
   (a) providing a passive gas sampling apparatus for detecting carbon monoxide, comprising
       (1) a shell enclosing an adsorbent, said adsorbent comprising a zeolite; and
       (2) a diffusion tube extending through said shell and having (i) an inlet opening means outside said shell, through which carbon monoxide may enter said diffusion tube, and (ii) an outlet opening inside said shell, said outlet opening being embedded in said adsorbent;
   (b) exposing said apparatus to said gas sample for a period of time, and
   (c) determining the concentration of said carbon monoxide in said gas sample by subjecting said adsorbent to conditions whereby said carbon monoxide is released from said adsorbent, and measuring the amount of said carbon monoxide so released.

2. The method of claim 1, wherein said measurement of the amount of said carbon monoxide is accomplished by a method comprising:
   (1) passing said released carbon monoxide over a gas chromatography separation apparatus,
   (2) catalytic reduction of said released carbon monoxide, and
   (3) determination, by flame ionization detector, of the molar amount of carbon monoxide so reduced.

* * * * *

UNITED STATES PATENT AND TRADEMARK OFFICE
CERTIFICATE OF CORRECTION

PATENT NO. : 5,168,068
DATED : December 1, 1992
INVENTOR(S) : Yukio Yanagisawa, et. al.

It is certified that error appears in the above-indentified patent and that said Letters Patent is hereby corrected as shown below:

Column 1, line 6, insert--This invention was made with government support under Grant No. RR 05446 awarded by the National Institutes of Health. The government has certain rights in the invention.--

Signed and Sealed this

First Day of August, 1995

Attest:

BRUCE LEHMAN

Attesting Officer

Commissioner of Patents and Trademarks